US006120490A

United States Patent [19]

Neftel

[11] Patent Number: 6,120,490

[45] Date of Patent: Sep. 19, 2000

[54] PIERCING PIN FOR AN INFUSION SYSTEM

[75] Inventor: Frédéric Neftel, Lausanne, Switzerland

[73] Assignee: Debiotech S.A., Lausanne, Switzerland

[21] Appl. No.: 08/983,312

[22] PCT Filed: Jul. 8, 1996

[86] PCT No.: PCT/FR96/01063

§ 371 Date: Jan. 9, 1998

§ 102(e) Date: Jan. 9, 1998

[87] PCT Pub. No.: WO97/02853

PCT Pub. Date: Jan. 30, 1997

[30] Foreign Application Priority Data

Jul. 11, 1995 [FR] France .................................. 95 08347

[51] Int. Cl.[7] .................................................. A61M 37/00

[52] U.S. Cl. .............................. 604/411; 604/414; 604/87

[58] Field of Search ....................... 604/85, 86, 239–241, 604/403, 411–415, 905; 141/27, 329, 330

[56] References Cited

U.S. PATENT DOCUMENTS 4,589,879 5/1986 Pearson .

FOREIGN PATENT DOCUMENTS

WO 87/02239 2/1987 WIPO .
WO 93/02724 2/1993 WIPO .
WO 94/08549 4/1994 WIPO .

*Primary Examiner*—Corrine McDermott
*Assistant Examiner*—David J. Cho
*Attorney, Agent, or Firm*—Wolf, Greenfield & Sacks, P.C.

[57] ABSTRACT

The invention relates to a piercing pin (10) for perfusion purposes to pierce the resilient capsule of a bottle and allow liquid to flow from the bottle (44) to a perfusion system. The piercing pin (10) for perfusion purposes is constituted by a pin body (30) having a longitudinal projection (36) including at least one internal duct (**37*a*, 37*b*), and piercing means (20) including an internal duct (25) extending said internal duct (37*a*, 37*b*) of the longitudinal projection (36), said piercing means (20) are removable and are connected to said longitudinal projection (36) by temporary fastening means (28, 38) for transmitting piercing force to said longitudinal projection (36) and for coming apart from said longitudinal projection (36**) when the pin is withdrawn from the bottle. The piercing pin can thus be used once only.

14 Claims, 3 Drawing Sheets

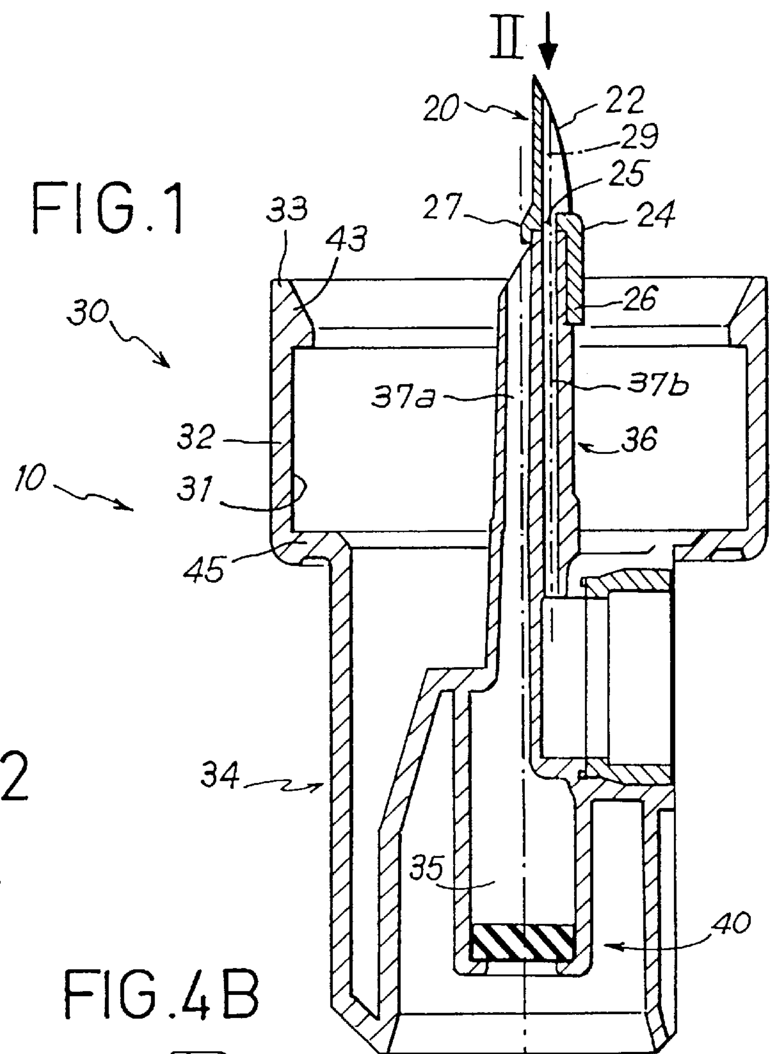
FIG.1
FIG. 2
FIG.4B
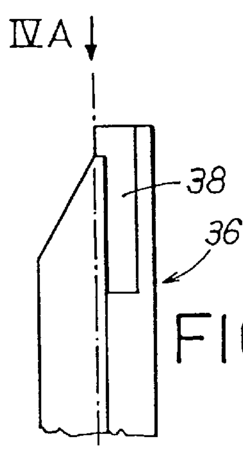
FIG.3A
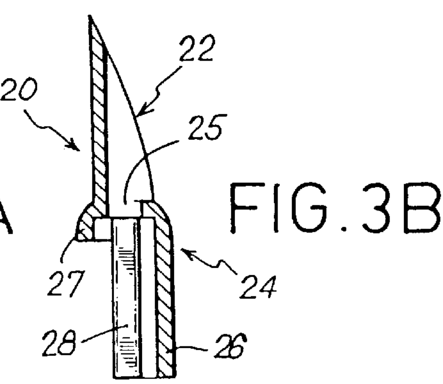
FIG.3B
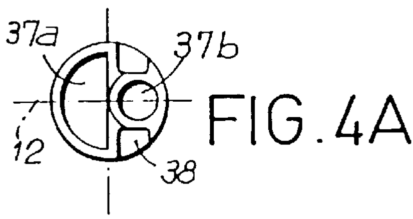
FIG.4A 44
20
14
42
46

20
26
46

PIERCING PIN FOR AN INFUSION SYSTEM

BACKGROUND OF THE INVENTION

1. Field of the Invention

The present invention relates to a piercing pin for perfusion purposes that can be used once only.

2. Description of the Related Art

A piercing pin for perfusion purposes is essentially constituted by a tip and a pin body having a through duct for conveying the flow of perfusion liquid.

When the perfusion system is connected to the perfusion bottle, the tip of the piercing pin pierces the resilient capsule of the perfusion bottle and the pin body is connected to the perfusion system, thereby allowing medication contained in the perfusion bottle to be infused slowly and continuously into the body of the patient.

A piercing pin for perfusion purposes is known that is made in such a manner that multiple successive uses thereof are possible.

Unfortunately, such a pin is sterile on first use only, and unless it is resterilized there is a risk of contamination during subsequent use.

The pin can thus be contaminated firstly at its tip, by the cap, the capsule, or the substance in the perfusion bottle, or subsequently the pin body can be contaminated by any part of the perfusion system or by the patient.

Another drawback of the prior art piercing pin for perfusion purposes is described below.

The tip of the piercing pin for perfusion purposes is designed to pierce the resilient capsule of the cap of the perfusion bottle and to guide the medication towards the perfusion system by means of an internal duct. When the piercing pin is used on successive occasions, its tip will in succession pierce the capsule of a new perfusion bottle, be pushed into the bottle, and subsequently be withdrawn from the bottle before being used again. Multiple piercing operations blunt the bevelled end of the tip of the pin, thereby making it less effective. In addition, particles of plastic due to said wear, or of rubber resulting from the use of a blunt tip, can pass into the internal duct of the pin and be injected into the patient unless retaining means such as an appropriate filter are provided in the perfusion system.

In order to avoid the above-mentioned drawbacks, there is considerable demand for a piercing pin for perfusion purposes to be developed that is incapable of being reused, however such a piercing pin has not yet been proposed.

BRIEF SUMMARY OF THE INVENTION

Consequently, the object of the present invention is to provide a piercing pin for perfusion purposes that can be used once only.

According to the present invention, this object is achieved by a single use piercing pin for perfusion purposes constituted by a pin body forming a main hollow portion, a longitudinal projection extending said main portion and including at least one internal duct, and piercing means for piercing a resilient capsule of a perfusion bottle and including an internal duct extending said internal duct of the longitudinal projection, in which the following improvements are provided:

said piercing means are constituted by a part that is removable from said longitudinal projection and that is connected to said longitudinal projection by temporary fastening means such that, when said piercing means pierce said capsule, said piercing means transmit the piercing force to said longitudinal projection, and such that, when said piercing means and said longitudinal projection pass through said capsule, said piercing means remain fastened to said longitudinal projection;

said perforation means also have at least one extension likewise capable of passing through said capsule; and said extension and said temporary fastening means enable said piercing means to be separated from said longitudinal projection when the pin is withdrawn from the bottle such that said piercing means remain inside the perfusion bottle.

The invention will be better understood and secondary characteristics and advantages thereof will appear on reading the following description of an embodiment given below by way of example.

Naturally the description and the drawings are given purely by way of non-limiting indication.

BRIEF DESCRIPTION OF THE SEVERAL VIEWS OF THE DRAWINGS

Reference is made to the accompanying drawings, in which:

FIG. 1 is an axial section view of a piercing pin of the invention;

FIG. 2 is a diagrammatic fragmentary front view seen in direction II on FIG. 1;

FIG. 3A is a fragmentary side view of the longitudinal projection from the body of the piercing pin;

FIG. 3B is an axial section view of the tip of the pin on III—III of FIG. 4B;

FIG. 4A is a diagrammatic front view of the end of the longitudinal projection from the body of the piercing pin in direction IVA on FIG. 3A;

FIG. 4B is a diagrammatic back view of the tip of the pin in direction IVB on FIG. 3B;

Figure 5:
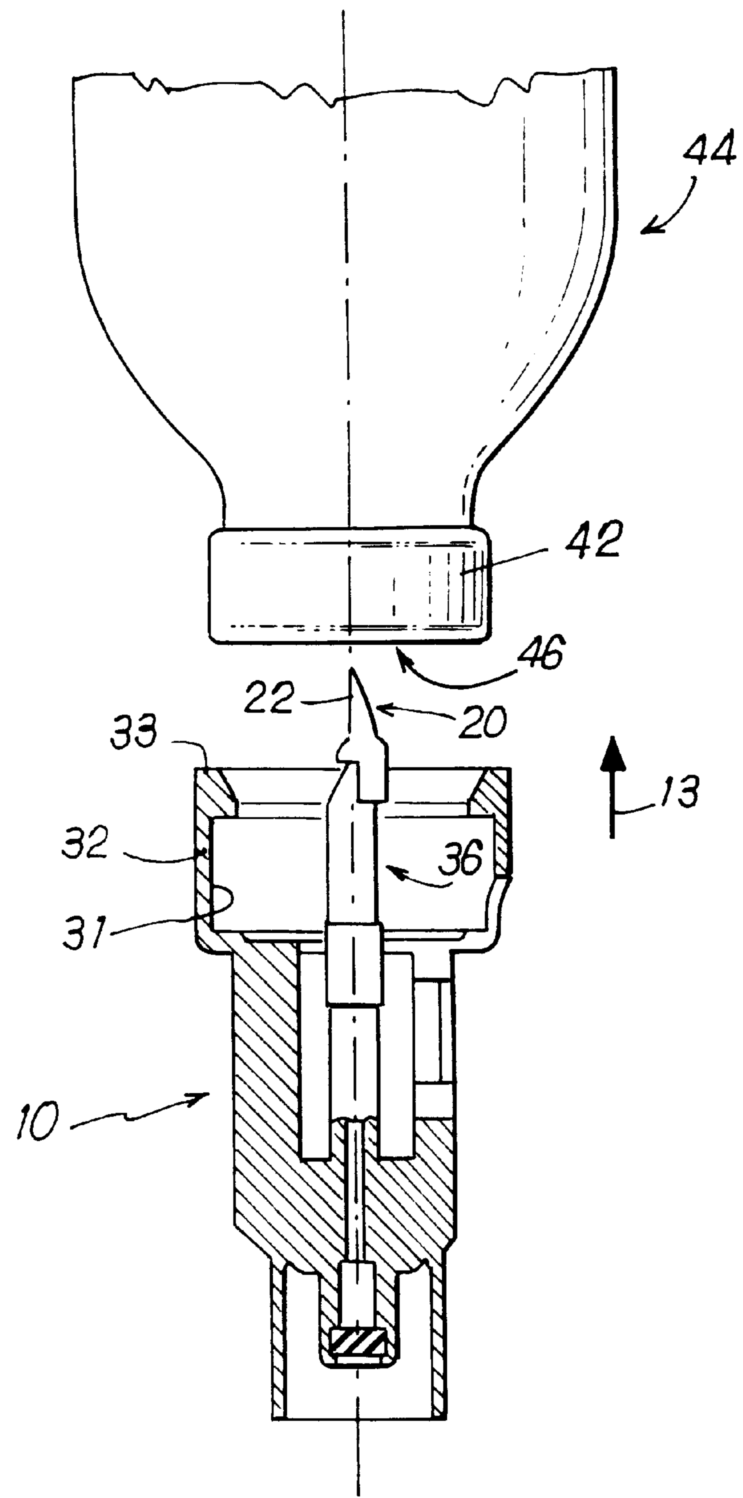
FIG. 5 is a fragmentary axial section view of the piercing pin and the perfusion bottle before the tip of the pin has pierced the cap of the bottle.

The piercing pin 10 shown in FIG. 1 comprises:

- a removable hollow tip 20 constituting piercing means and formed by a base 24 and a bevelled end 22 for piercing the resilient capsule 46 of the cap 42 of a perfusion bottle 44; and
- a pin body 30 made up of a hollow main portion 34, a longitudinal projection 36 extending said main portion 34, and an annular side wall 32 extending said main portion 34 and surrounding said longitudinal projection 36, at least in part. The pin body 30 is a cylinder of circular section and the outside diameter of its side wall 32 is larger than that of the main portion 34. The internal periphery of the side wall 32 is also a cylinder of circular section and surrounds the longitudinal projection 36 whose external periphery is essentially cylindrical and of circular section. The main portion 34, the side wall 32, and the longitudinal projection 36 are in line on and coaxial about a first longitudinal axis 39.

The base 24 of the hollow tip 20 is designed to be fastened temporarily to the longitudinal projection 36 from the body of the pin 30.

To this end, said temporary fastening means 28, 38 are disposed on said base 24 of the hollow tip 20 and also on a free end of said longitudinal projection 36 from the pin body 30.

As can be seen in FIGS. 3A, 3B, and 4A, 4B, in accordance with an advantageous characteristic, said temporary fastening means are constituted by a guide system having a first slideway 38 on the free end of the longitudinal projection 36 and a second slideway 28 on said base 24, said second slideway 28 constituting an element that is complementary to said first slideway 38, said first and second slideways 28 and 38 being designed to co-operate for reversibly positioning said hollow tip 20 on said cylindrical projection 36 of the pin body 30. Also, provision is made for the profile of said second slideway 28 to be T-shaped.

In this embodiment, the first and second slideways 28 and 38 co-operate in reversible rectilinear translation movement, thus enabling the hollow tip 20 to be guided in translation relative to the end of the longitudinal projection 36.

The first slideway 38 is made up of two longitudinal grooves, disposed symmetrically to each other at the periphery of the longitudinal projection 36. The inside walls of these grooves prevent any rotary movement of the hollow tip 20 relative to the longitudinal projection 36.

The second slideway 28 has an inner periphery which is complementary to the outer periphery of said first slideway 38, in particular it has two longitudinal projections that are symmetrical relative to each other about a vertical longitudinal plane of symmetry or midplane 12 which also defines a plane of orthogonal symmetry for the piercing pin 10 as a whole.

The longitudinal projection 36 is cylindrical, of circular section, with the exception of its free end where the first slideway 38 is situated.

According to an essential characteristic of the invention, in order to prevent the pin 10 from being reused, a removable tip 20 is provided which necessarily becomes detached from the pin body 30 when the pin is separated from the perfusion bottle. To this end, the hollow tip also has an extension 26 which does not hinder the tip 20 in piercing and then passing through the capsule 46 of the perfusion bottle 44. The extension 26 consists in a projection 26 that slightly overhangs the outer periphery of the surface following said projection 26 going towards the main portion 34 of the pin body when said piercing means 20 are positioned on the pin body 30 by said temporary fastening means 28, 38, such that the capsule 46 comes into abutment against said projection 26 when the pin 10 is withdrawn from the bottle 44.

With reference to FIG. 1, it can be seen that the projection 26 projects radially from a portion of the outer periphery of the cylindrical longitudinal projection 36, said portion of the outer periphery in the embodiment shown constituting the surface following the projection 26 going towards the main portion 34 of the pin body when the tip 20 is connected to the pin body 30. The tip 20 defines a second longitudinal axis 29 parallel to said first longitudinal axis 39 when the tip 20 is fitted to the pin body 30.

In the embodiment shown, the projection 26 follows the second slideway 28 and constitutes an external extension thereof. As can be seen in FIGS. 2 and 4B, the projection is in the form of a length of an oval section hollow half-cylinder whose longitudinal edges are folded inwards and form the longitudinal projections of the second slideway 28. The free end of the projection 26 is plane and perpendicular to the second longitudinal axis 29 and it forms a plane surface against which the inside face of the capsule 46 bears when the pin 10 is separated from the perfusion bottle 44. The capsule 46 thus prevents the hollow tip 20 returning, given that the tip comes apart easily from the pin body 30 because of the slideway guide system, thus causing the tip to drop off in the bottle.

A perfusion bottle 44 containing the liquid to be perfused essentially comprises a bottle, e.g. made of glass, a resilient capsule 46, and a cap 42. The perfusion bottle 44 shown in part in FIGS. 5 to 7 includes a cap 42 surrounding the outer periphery of its neck and partially closing the opening of the bottle, while leaving access to the central zone of the opening through which the tip 20 of the pin 10 is to pass. A hollow cylinder of circular section made of resilient material covers the inside of the neck of the perfusion bottle and also forms the resilient capsule 46 that provides a thin wall completely closing the cylinder, thereby constituting the element which closes the perfusion bottle. The front face of the capsule 46 is in plane contact with the back face of the portion of the cap 42 which partially closes the opening of the bottle.

The outer periphery of the cap 42 is circularly cylindrical in shape and the back end thereof has a lip projecting inwardly towards the outside of the glass bottle.

The side wall of the pin body is designed to receive the outer periphery of the cap 42 of the perfusion bottle, and thereby serve as a support element for the perfusion bottle. Firstly, the side wall 32 must posses a degree of resilience and must be capable of holding the cap 42 in place so that it does not become separated in untimely manner from the piercing pin 10. To this end, said side wall 32 of the pin body 30 is provided with uniformly spaced-apart longitudinal slots extending over the full length of said side wall 32.

The free end 33 of said side wall 32 includes a rib on its inside face projecting radially inwards so that said rib 43 serves as a catch or as a stop element for engaging the edge of the back face of the cap 42 of the perfusion bottle 44 when said cap 42 is fully engaged into said pin body 30 and when said perfusion bottle has any tendency to move longitudinally away from the pin 10.

Thus, when the perfusion bottle 44 is in position on the pin 10, the side wall 32 enlarges as permitted by the slots, and surrounds the cap 42, and then, when the cap 42 is completely surrounded by the side wall 32, the side wall 32 returns to its initial shape and the rib 43 bears against the back edge of the cap 42 (FIG. 6) to prevent the bottle 44 from being separated axially from the pin 10.

In addition, to prevent further engagement axial movement between the bottle 44 and the pin 10, it is advantageous to ensure that the periphery of the inside face connecting said side wall 32 to said main portion 34 of the pin body 30 presents an abutment 45 suitable for co-operating with the end face of said cap 42 of the perfusion bottle when said cap is fully engaged in said pin body 30.

A suitable technique for manufacturing the body provides for the main portion 34 thereof to have a circularly symmetrical outer periphery around a first longitudinal axis 39:

the inner periphery 31 of said side wall 32 is circularly cylindrical about said first longitudinal axis 39; and the outer periphery of said cap 42 of the perfusion bottle 44 is circularly cylindrical, having a diameter that is smaller than or equal to the diameter of the inner periphery of said side wall 32.

Another aspect of the invention is described below and relates to the ducts along which the perfusion liquid flows. The liquid must flow from the perfusion bottle through the pin and be guided towards the perfusion system. This aspect is not described in detail herein, but is performed by the back portion 40 of the pin body 30, said portion 40 carrying means for co-operating with the element of the perfusion system that is to be connected to the perfusion bottle 44 via the pin 10, e.g. a hose. This back portion 40 of the pin body 30 incorporates the back end of a duct that passes axially through the pin body 30 and that serves to guide the flow of perfusion liquid. This duct is centered on the first longitudinal axis 39 and comprises the internal duct 35 of the main portion 34 of the pin body 30 together with its extension, i.e. a first internal duct 37*a* in the longitudinal projection 36. As shown in FIG. 1, the main portion 34 of the pin body 30 includes an internal duct 35 extending said internal duct 37*a*, 37*b* of the longitudinal projection 36, the end of said internal duct 35 of the main portion being closed by a septum of pre-slit latex.

This septum may be made of rubber, and it need not be pre-slit, however it serves to guarantee that the assembly constituted by the piercing pin 10 of the invention and the perfusion bottle 44 is leakproof. When the bottle is in position on the pin, liquid flows through the internal ducts 37*a* and 35 of the pin body 30, and because of the septum, the liquid does not flow any further. Thereafter, the pin 10 is connected to the perfusion system: another hollow tip (not shown) pierces said septum so that the perfusion liquid can flow into the entire perfusion system. When perfusion is terminated, the bottle is separated from the piercing pin and the piercing pin is separated from the perfusion system: since the septum is flexible, it recloses its slit and prevents any liquid that remains in the internal duct 35 of the main portion 34 of the pin body 30 from flowing out.

The hollow tip 20 includes a duct 25 centered on the second longitudinal axis 29. The longitudinal projection has a second internal duct 37*b* which, when the tip 20 is in position on the longitudinal projection 36 of the pin body via the temporary fastening means 28, 38, is centered on the second longitudinal axis 29 and is in line with the internal duct 25 of the tip 20.

This second internal duct 37*b* can be connected to a ventilation aperture or air intake beside its back end and it communicates with the internal duct 25 of the tip 20; these two internal ducts 37*b* and 25 can thus guide a flow of filtered outside air into the perfusion bottle so as to allow the bottle to empty out its contents. The base 24 of the tip 20 must not close the leading end of the first internal duct 37*a* of the longitudinal projection 36, and for this purpose the leading end of the longitudinal projection 36 is bevelled on the side where the first duct 37*a* of the longitudinal projection 36 opens out (FIG. 1). In addition, the base 24 of the tip 20 carries a projection 27 whose outer profile projects very slightly over the end of the first internal duct 37*a*, with the inner profile thereof being complementary to a portion of the outer profile of the second internal duct 37*b*, the second internal duct 37*b* extending beyond the first internal duct 37*a*. The inner profile of the projection 27 serves to prevent any movement in transverse translation of the tip 20 relative to the longitudinal projection 36 in the transverse direction defined by the midplane 12.

By way of example, the piercing pin for perfusion purposes 10 of the invention can be made of injection molded plastics material. The successive steps in which the pin is used are shown in FIGS. 5 to 7.

Figure 6:
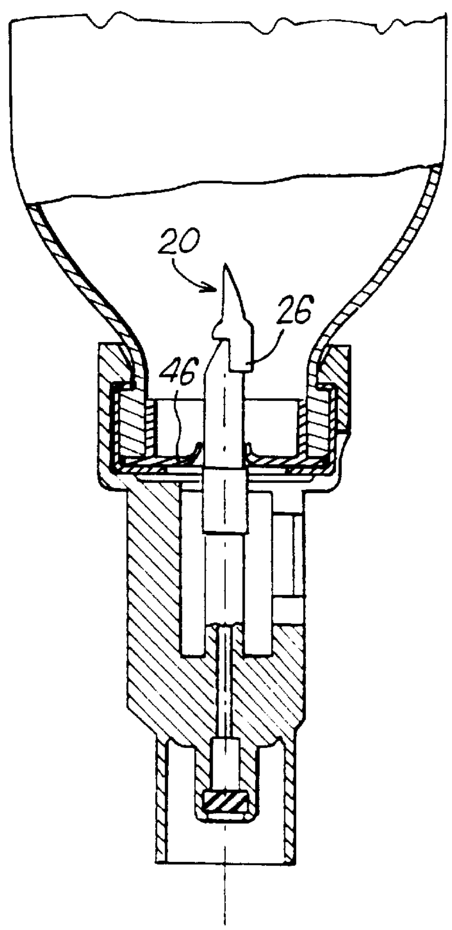
FIG. 6 is analogous to FIG. 5 but shows the relative position of the pin and of the cap after the cap has been fully pierced by the pin.

FIG. 5 shows the bottle 44 and the pin 10 before they come into contact: the central portion of the front face of the cap 42 faces the bevelled end of the tip 20 and the longitudinal axis of the bottle 44 is parallel to, and substantially coincident with, the first longitudinal axis 39 of the pin body.

Thereafter, the pin 10 is moved along arrow 13 in FIG. 5 and the bevelled end 22 of the tip 20 perforates the resilient capsule 46 of the bottle 44 with the tip 20 and the major portion of the longitudinal projection 36 penetrating into the bottle 44. Once the cap 42 has been fully engaged in the leading portion of the pin body 10 (FIG. 6), any significant movement of the cap 42 relative to the pin body 30 is prevented in the transverse direction by the inner periphery 31 of the side wall 32, and axially because of the front and back stops constituted respectively by the abutment 45 and the inner transverse edge of the rib 43. The capsule 46 has been pierced and the lip of the pierced slit is folded back against the outer periphery of the longitudinal projection 36. A bottle and piercing pin assembly is thus obtained which is stable and suitable for performing perfusion.

Figure 7:
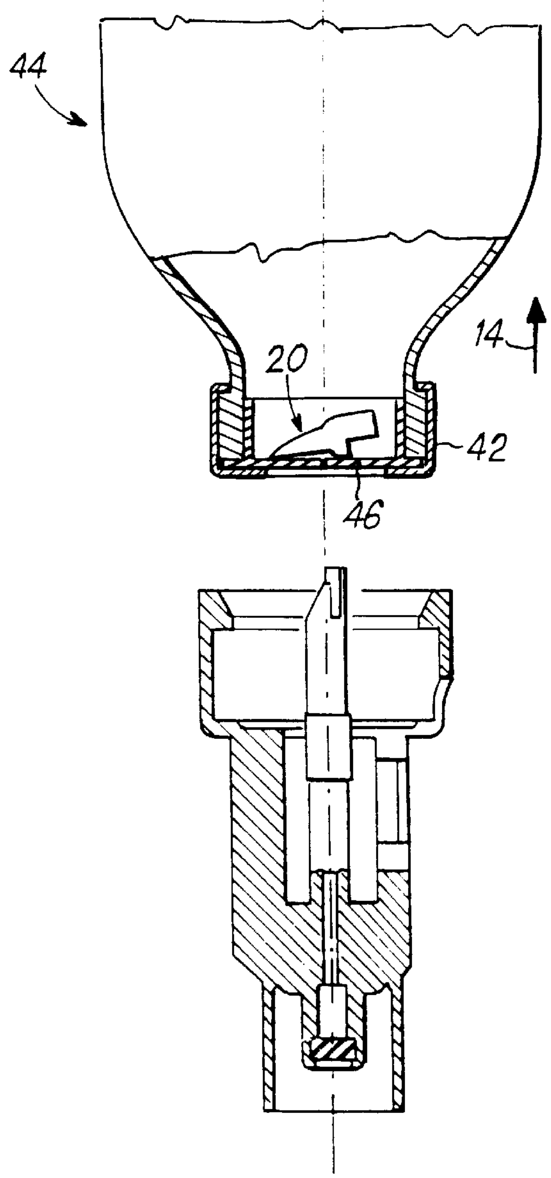
FIG. 7 is analogous to FIG. 5, but shows the perfusion bottle and the piercing pin after they have been separated from each other.

When perfusion has been completed, the empty or partially empty perfusion bottle 44 is pulled more or less axially in the direction of arrow 14 in FIG. 7.

The side wall 32, which is made resilient by its longitudinal slots, enlarges to release the cap 42 and when the folded-over lip of the slit in the capsule 46 comes into contact with the plane transverse back face of the projection 26, the tip 20 comes to bear against the capsule 46. In this way the capsule 46 retains the tip 20 in the bottle and the lip of the slit folds back to reclose the capsule: the tip 20 is held captive inside the perfusion bottle 44 and the piercing pin 10 for perfusion purposes of the invention cannot be reused.

I claim:

1. A single use piercing pin for piercing the resilient capsule of a perfusion bottle, said piercing pin comprising:

a pin body including a main hollow portion and a longitudinal projection extending from said main portion, said projection being provided with a first internal duct and a second internal duct, the main portion of the pin body defining a first longitudinal axis around which said first internal duct of the longitudinal projection is centered, said first internal duct being an extension of an internal duct of the main portion of the pin body;

piercing means removable from said pin body for piercing said resilient capsule, said piercing means being provided with an internal passage, the internal passage of said piercing means defining a second longitudinal axis; and fastening means for temporarily fastening said piercing means to said longitudinal projection so that said second internal duct of said projection extends from said internal passage of said piercing means and so that said second internal duct is centered on said second longitudinal axis, said fastening means including means for transmitting a force to the piercing means when a force is applied in a first direction for piercing said resilient capsule so that said piercing means pass through said capsule and penetrate inside said bottle, and means for allowing said piercing means to be disconnected from said longitudinal projection when a force is applied to said bottle in a second direction opposite to said first direction for separating said piercing pin from said bottle, whereby said piercing means remain in said bottle, said second internal duct allowing filtered outside air to pass into the perfusion bottle.

2. A piercing pin according to claim 1, wherein said piercing means comprise a hollow tip having a free end which is beveled for piercing said capsule and a base designed to temporarily cooperate with said longitudinal extension of the pin body.

3. A piercing pin for perfusion purposes according to claim 2 wherein said temporary fastening means are disposed firstly on said base of the hollow tip and secondly on a free end of said longitudinal projection of the pin body.

4. A piercing pin for perfusion purposes according to claim 3, wherein said temporary fastening means are constituted by a guide system comprising a first slideway on the free end of the longitudinal projection and a second slideway on said base, said second slideway being complementary to said first slideway, said first and second slideways being designed to co-operate for the purpose of reversibly positioning said hollow tip on said cylindrical projection of the pin body.

5. A piercing pin for perfusion purposes according to claim 5, wherein the profile of said second slideway is T-shaped.

6. A piercing pin according to claim 1, wherein said piercing means comprise an extension portion designated to pass through the capsule of said bottle when the force is applied to the bottle in the first direction.

7. A piercing pin for perfusion purposes according to claim 6 wherein the extension consists of a projection laterally overhanging the outer periphery of the surface following said projection going towards the main portion of the pin body when said piercing means are in position on the pin body via said temporary fastening means, such that the capsule of the bottle comes into abutment against said projection when the piercing pin is withdrawn from the bottle.

8. A piercing pin for perfusion purposes according to claim 1 wherein the main portion of the pin body includes an internal duct extending from said internal duct of the longitudinal projection, the end of said internal duct of the main portion being closed by a septum of pre-slit latex.

9. A single use piercing pin for piercing the resilient capsule of a perfusion bottle, said piercing pin comprising;

a pin body including a side wall, a main hollow portion, an inside face connecting the side wall to the main portion and a longitudinal projection extending from said main portion, said projection being provided with at least one internal duct;

piercing means removable from said pin body for piercing said resilient capsule, said piercing means being provided with an internal passage;

fastening means for temporarily fastening said piercing means to said longitudinal projection so that said internal passage of said piercing means extends from said internal duct of said projection, said piercing means including means for transmitting a force to the piercing means when a force is applied in a first direction for piercing said resilient capsule so that said piercing means pass through said capsule and penetrate inside said bottle, and means for allowing said piercing means to be disconnected from said longitudinal projection when a force is applied to said bottle in a second direction opposite to said first direction for separating said piercing pin from said bottle, whereby said piercing means remain inside said bottle; and an abutment disposed on a periphery of the inside face connecting the side wall to the main portion of the pin body, said abutment cooperating with an end face of a cap of the perfusion bottle when the cap is fully engaged within said pin body.

10. A piercing pin according to claim 9, wherein the sidewall of the pin body extends from said main portion of the pin body and surround s, at least in part, said longitudinal projection.

11. A piercing pin purposes according to claim 10, wherein said side wall of the pin body has longitudinal slots that are regularly spaced apart extending along the entire length of said side wall and the free end of said side wall includes, on its inside face, a rib projecting radially so that said rib serves as a catch element for engaging the back face of the cap of the perfusion bottle when said cap is fully engaged in said pin body and when said perfusion bottle has any tendency to move longitudinally away from the piercing pin.

12. A piercing pin according to claim 11 wherein said side wall of said pin body is structured to support the perfusion bottle and to hold the perfusion bottle both radially and axially.

13. A single use piercing pin for piercing the resilient capsule of a perfusion bottle, said piercing pin comprising:

a pin body including a main hollow portion and a longitudinal projection extending from said main portion, said projection being provided with at least one internal duct;

piercing means removable from said pin body for piercing said resilient capsule, said piercing means being provided with an internal passage, said piercing means comprising a hollow tip having a free end which is beveled for piercing said capsule and a base designed to temporarily cooperate with said longitudinal projection;

fastening means for temporarily fastening said piercing means to said longitudinal projections so that said internal passage of said piercing means extends from said internal duct of said projection, said fastening means including means for transmitting a force to the piercing means when a force is applied in a first direction for piercing said resilient capsule so that said piercing means pass through said capsule and penetrate inside said bottle, and means for allowing said piercing means to be disconnected from said longitudinal projection when a force is applied to said bottle in a second direction opposite to said first direction for separating said piercing pin from said bottle, whereby said piercing means remain inside said bottle, said fastening means comprising a guide system comprising a first slideway disposed on a free end of the longitudinal projection and a second slideway disposed on said base of said piercing means, said second slideway being complementary to said first slideway, said first and second slideways being designed to cooperate for the purpose of reversibly positioning said hollow tip on said longitudinal projection of said pin body.

14. A single use piercing pin for piercing the resilient capsule of a perfusion bottle, said piercing pin comprising:

a pin body including a main hollow portion and a longitudinal projection extending from said main portion, said projection being provided with at least one internal duct;

piercing means removable from said pin body for piercing said resilient capsule, said piercing means being provided with an internal passage, said piercing means comprising an extension portion designed to pass through the capsule of said bottle when force is applied to the bottle in a first direction; and fastening means for temporarily fastening said piercing means to said longitudinal projection so that said internal passage of said piercing means extends from said internal duct of said projection, said fastening means including means for transmitting a force to the piercing means when a force is applied in the first direction for piercing said resilient capsule so that said piercing means pass through said capsule and penetrate inside said bottle, and means for allowing said piercing means to be disconnected from said longitudinal projection when a force is applied to said bottle in a second direction opposite to said first direction for separating said piercing pin from said bottle, whereby said piercing means remain inside said bottle;

said extension portion of said piercing means comprising a projection laterally overhanging an outer periphery of a surface of said pin body after said projection going towards said main portion of said pin body when said piercing means are in position on said pin body via said temporary fastening means, such that the capsule of the bottle comes into abutment against said projection of said piercing means when said piercing pin is withdrawn from the bottle.

* * * * *